United States Patent [19]

Heitlinger et al.

[11] 4,324,546
[45] Apr. 13, 1982

[54] METHOD FOR THE MANUFACTURE OF DENTURES AND DEVICE FOR CARRYING OUT THE METHOD

[76] Inventors: Paul Heitlinger, Chemnitzer Strasse 15, 6054 Rodgau 3; Fritz Rodder, Schulstrasse 1, 6273 Waldems/Esch, both of Fed. Rep. of Germany

[21] Appl. No.: 167,974

[22] Filed: Jul. 14, 1980

[30] Foreign Application Priority Data

Sep. 12, 1979 [DE] Fed. Rep. of Germany ....... 2936847

[51] Int. Cl.³ .............................................. A61C 13/00
[52] U.S. Cl. ...................................... 433/25; 433/213
[58] Field of Search ..................... 433/213, 214, 54, 25

[56] References Cited

U.S. PATENT DOCUMENTS 3,100,344  8/1963  Sharp .
3,861,044  1/1975  Swinson .............................. 433/213

OTHER PUBLICATIONS

"A Digital Optoelectronic Method for Recording Mandibular Movement in Association with Oral Electromyograms and Temporomandibular Joint Noises," *Medical and Biological Engineering*, Sep. 1974.

*Primary Examiner*—Robert Peshock
*Attorney, Agent, or Firm*—Biebel, French & Nauman

[57] ABSTRACT

For the manufacture of a denture, or artifical teeth, the prepared tooth stump is reproduced as a working model, and the substitute piece, suitably conformed to the working model, is shaped by hand. In order to facilitate the dentist's work, and at the same time attain great accuracy, it is provided that reproduction of the tooth stump is accomplished electro-optically in such a manner that surface-information signals corresponding to the tooth stump are generated and are converted in an electronic computer into electrical and/or magnetic control signals with the aid of which a milling machine automatically mills the working model out of a block of material; and/or that the positive substitute piece is milled by the milling machine from a block of material in accordance with control signals which are derived from surface-information signals which are electro-optically derived from the hand-shaped substitute or replacement model. The device for carrying out the method is characterized by an optical reproduction-photographing device for sweeping over the portion of the tooth in question; furthermore, by an electronic computer for sensing and evaluating the surface-information signals generated by a reproducing device, a milling machine, and/or if necessary, a storage apparatus.

16 Claims, 6 Drawing Figures

METHOD FOR THE MANUFACTURE OF DENTURES AND DEVICE FOR CARRYING OUT THE METHOD

The invention relates to a method for the manufacture of artificial teeth or dentures in which the prepared stump of a tooth or teeth is reproduced in a working model, and the substitute piece, adapted by hand to correspond to the working model is formed, and also relates to a device for carrying out the method.

Numerous methods of the above-cited type are known for the manufacture of artificial teeth. The ability to produce an exactly-seated crown, as an artificial tooth, depends on control of the copying technique. The three most common methods are copying, taking an impression with silicone or rubber composition, or with hydrocolloid, as well as with a copper ring and molding material. The dentist's work and education are made difficult by the fact that he must unconditionally command a number of methods for taking an impression. Also, for taking an impression, the elastic material, for example, the gums, must be drawn back sufficiently that the later-prepared teeth or tooth stumps will be grasped by it. Retraction of the soft part requires a not-significant expenditure of labor.

Furthermore, in cases in which several crowns are required in the front area, it is important to prepare the teeth and then provide them with a well-seated temporary substitute. With the aforesaid measures, several sittings and impressions are necessary.

A new or impression method is a method using cooper ring and molding material. The drawback of the material utilized consists in the fact that, with it, an impression of the entire row of teeth cannot be taken at the same time, an impression of underneath parts cannot be taken, and the fairly warm molding material can lead to irritation of the pulp. Formation and insertion of the ring must be done with extraordinary caution in order that the soft part will not be damaged. In the case of multiple supporting (or pillar) teeth, taking an impression is very time consuming.

A second method is performed with rubber composition material. In the last fifty years, three types of elastic or impression material on a rubber base have been developed with polysulfide, silicone, and polyether rubber. Silicone rubber and polyether rubber do indeed have a better color and a more agreeable taste and are more acceptable from the esthetic point of view, but they are not utilized as frequently as polysulfide rubber.

With the use of elastic-rubber materials, the expenditure of time is great. However, the principal drawback is that the retraction of the soft parts and complete dryness of the area in question are necessary, since the molding material can be shifted out of position very easily.

In a series of experiments by Ferguson and Strode with rubber-composition impressions, 10% of 250 impressions had inclusions of air below the surface, which, after the pressure is released, cause expanding depressions in the matrix and protrusions on the crown. Premature removal of pressure is a frequent cause of failures. The time between the beginning of mixing and the taking of the impression should amount to at least ten, better fifteen, minutes. Here, however, errors and false measurements can take place very easily.

A third known method is preformed with reversible hydrocolloid. This impression material has been utilized since about 1925. It becomes fluid upon being heated and returns to its gel state after cooling off. The principal drawback of hydrocolloid is the necessity of making or casting of the impression immediately. Since hydrocolloid does not displace the gums, retraction of the soft part and meticulous drying are indispensable for accuracy of reproduction of the marginal area. The difficulties and the expenditure of time required here are well understood.

The following guidelines must be followed in order to guarantee accuracy of the impression: The spoon material must first be tempered in order that it will assume a certain jelly-like consistency. In that way, the viscosity will be increased, and temperature shock to the teeth will be reduced. In addition, the impression spoon must have a layer of material three mm. thick occlusally and laterally, in order that sufficient accuracy will be assured.

Aside from the unpleasant odor of the rubber composition material, this method is correspondingly difficult, time-consuming and complicated. At least five minutes are required for an impression of the entire row of teeth. In order to avoid alterations of form, the model must be cast within fifteen to forty minutes. The difficulties of the known methods for manufacturing artificial teeth, which are not conceivable without the impression method, are recognized.

However, still further difficulties arise in connection with temporary measures. Every patient is concerned about his appearance after preparation for the crown has been completed. The old rule that a temporary or provisional substitute does not have to be as beautiful as the permanent substitute is plainly false. Well-made and meticulously-fitted substitute shapes fulfill a functional and an esthetic purpose.

The main problem of any provisional substitute shape is optimal protection for the tooth and the tissue surrounding it for the time until the final substitute is finished. The temporary substitute offers the dentist the possibility of making it exactly clear how the final substitute must appear with regard to its shape and size as well as color, to a certain extent. Besides, the temporary substitute makes it possible to modify the provisional arrangement before the final substitute is manufactured. Also, the provisional substitute protects the pulp from chemical, thermic, and mechanical influences. One of the older methods, still in use today, is the alginate technique for manufacturing a temporary acrylate substitute.

Even with the temporary substitute, at least one impression must first be taken for producing the working model of the prepared stump of the tooth; then a substitute model must be prepared by hand from wax or the like, and the temporary substitute must be modeled with its aid.

Therefore, the problem of the invention is the improvement of the known method for the manufacture of dentures with the aforementioned features and measures, as well as the creation of a device for carrying out such a method, with which the dentist's work is facilitated and at the same time greater accuracy is attained.

According to the invention, this problem is solved by the fact that reproduction of the stump of the tooth is accomplished electro-optically in such a manner that surface-information signals corresponding to the stump of the tooth are generated and are converted in an electronic computer into electrical and/or magnetic control signals, with the aid of which a milling machine automatically mills the working model out of a block of material; and in such a manner that the positive replacement piece is milled out of a block of material in accordance with control signals which are derived from surface-information signals which are derived electro-optically from the hand-formed substitute model. By means of the novel invention it is possible to reproduce the tooth stump with the adjacent maxillary areas, electro-optically; that is, to photograph them, to film them, or to reproduce them on a Roentgen plate. Surface information signals can be generated from such a reproduction, which corresponds to the stump of the tooth with the adjacent areas, a photograph or an X-ray picture being scanned, optically, for example. Manifestly, the distance from line to line permits extraordinarily great accuracy. Through the use of the measures according to the invention, difficulties no longer arise in making reproductions of the stump of the tooth accurate to one $\mu$. When the surface-information signals have been suitably generated by the corresponding scanner, they are entered into an electronic computer, in which they are converted into electrical and/or magnetic control signals. It is not necessary here to go into detail into the construction of the electronic computer, for which the current state of the art it is possible to encode, process, and decode suitable information signals. In this way, electromagnetic, electrical, or magnetic control signals can be obtained which are fed into a suitable control aggregate in a milling machine, which, controlled by these control signals, automatically mills out the desired working model from a block of material. For this, an abrasion-proof synthetic material, but also gypsum, a resin, or another desired material can be used, as long as the milling-away is assured. Consequently, a very precise working model can be produced in astonishing fashion without the cumbersome and partially inaccurate reproduction process.

Also, a positive substitute piece can be produced simultaneously, alternatively, or additionally through the teaching of the invention without the impression method. The milling machine mills the positive substitute piece—that is, either the temporary substitute piece or a bridge or the like, from a block of suitable material in accordance with control signals, which are similarly obtained as described above. They are derived from surface-information signals which, again, are derived electro-optically, for example, by photographing, filming, X-ray photographing or the like, from the hand-shaped substitute model. It is especially suitable if, in accordance with the invention, the electro-optical reproduction of the stump of the tooth and/or the substitute model is accomplished photogrammetrically or by means of Roentgen photographs, and if the surface-information signals are derived from a paper photo, an optical film, a Roentgen plate, or a video tape.

The most varied kinds of Roentgen apparatus for reproducing teeth and jawbones are known. For example, if a panorama Roentgen apparatus is improved and equipped in such a manner that the teeth appear on the Roentgen plate viewed not only from one side but also are photographed from below, from the other side, and overlapping, on a plurality of Roentgen plates, then the method of known photogrammetry can be used, so that the Roentgen photographs, subdivided into optionally-fine raster or coordinates, can be converted into such fine surface-information signals that therewith a very precise spatial description of the tooth or jawbone in question is at hand.

In the same way, however, one can reproduce the stump of the tooth or the prepared denture spatially by means of photographic pictures or by means of films. For this, the known method of photogrammetry is utilized. As is known, this is a method technique according to which photographic photograms can be produced, altered geometrically or structurally, and evaluated graphically or numerically. The fundamental methods for photogrammetry were developed almost exclusively in connection with the treatment of geodetic-measuring-technical problems.

Photogrammetry has significant meaning for topography, aerial photograph measurements being principally employed. In known manner, attention is paid to longitudinal and transverse overlapping of numerous photographs made one after another in succession of a flying body.

If this known method is utilized in dental technique, the prepared denture can be reproduced in astonishing fashion with extraordinary accuracy, very rapidly, and without burdensome treatment of the patient.

In accordance with the invention, it is suitable if the electrical and/or magnetic control signals are stored intermediately. The evaluated surface-information signals, which can then be used directly, to control the milling machine or indirectly after the intermediate storage, for re-selection, make possible the placing of spatial images with greatest accuracy in the smallest space. In passing, so to speak, the dentist can hold his patient's denture fast spatially and very accurately, feed the prepared signals to a storage device, and then recall them at any time. Also, the economic significance for dental-technical laboratories is recognized. Expense for material is smaller through the lack of many molding materials, less working force is used for modeling, and yet the dentist achieves substantially better accuracy so that a set of teeth produced by him—a bridge extending over a number of teeth, for example—can be accurately and immediately fitted into the patient's prepared denture and cemented in.

According to the invention, it is of further advantage if the surface-information signals can be evaluated for optical-visual reproduction on a video display apparatus. By means of techniques known in the field of electronics, it is possible to process the reproduction-information signals obtained through the aforementioned measure into electrical and/or magnetic data, which can be made optically visible on a video display apparatus without anything further. These measures facilitate the preparation of the patient's denture for the dentist, because without expense of material for molding materials, and without tedious engagements disagreeable to the patient, for hand-grinding between engagements, he can always ascertain and check the real state of affairs from all perspecitive, so that he can dispense with inspection with mirrors in the so-far customary manner as his sole aid. This method is especially useful when a number of teeth next to one another have to be prepared. Then he can set up various enlargements on the video display apparatus and check the parallel positioning, for example, which up to the present time he has been able to do only by eye measurement. The known method was inaccurate and time-consuming and in simple fashion becomes more accurate and quicker by means of the new method.

Furthermore, the invention is advantageous because various reproductions are shown simultaneously, optically visible, on the video display apparatus for purposes of comparison. Operating according to this method is especially serviceable for protecting the substance of the tooth, in order that irreparable failures will not originate as a result of the substance of the tooth being eroded in the wrong positions. For example, the ideal state of a prepared tooth or portion of a denture can be preprogrammed and stored in a computer. The dentist can deduce this ideal state from a photograph of the actual state of affairs if he allows for the desired grind-off of 1.8 or 0.8 mm., or any other amount of grind-off necessary. Then, in the processing in between times, checks can always be made as on a monitor, the actual state and the ideal theoretical state being projected one above the other on the projection screen, so that the dentist immediately recognizes at which points tooth substance must be removed and at which points not. Regulations of the denture can be promoted in this way, and a denture of twenty teeth is possible simultaneously with greatest accuracy and without danger.

The device for carrying out the method is characterized by an optical reproducing device for sweeping over the tooth parts concerned, and further by an electronic computer for sensing and evaluating the surface-information signals generated by the reproducing device; by a milling machine, and/or, if necessary, by a storage apparatus. The use of these known apparatuses in this sequence and for the aforementioned purpose is surprising. The dentist can make use of a generally-known technique and, with economically-replaceable means, achieve results whose equal has been sought for up to the present time with regard to rapidity, accuracy, agreeable treatment of the patient, etc.

It is of special advantage if, according to the invention, the optical reproductive device has a holder in the form of an impression spoon for a plurality of lenses, to which photo-conductive cables are secured, at the other end of which cables a source of light and a recording device are mounted with which an electronic sensing device is connected; and if a computer for evaluating and/or storing the surface-information signals is connected. The other alternative for the reproducing device—namely, the Roentgen panorama photographing apparatus—has been described above, it has to be supplemented in such a manner that the tooth part in question can be viewed from at least three sides. Only suitable motor drives need be provided with the aid of which various Roentgen photographs, mutually overlapping and directed from all sides of the space onto the stump of the tooth, are produced.

The other embodiment, with the purely optical photography or with films, can be constructed particularly advantageously and easily by inserting photoconductive cables likewise made of known fibrous material. With their aid, it is possible without anything further to bring the lenses into their place in such an area near to the teeth to be photographed that the entire upper or lower denture is photographed, for example, with one photograph. Then it is advantageous if an extinguishing device is connected to the optical reproducing device. It serves as a timer and wipes out various photographs in the manner of known photogrammetry. Here, also, the images are appropriately arranged to be overlapping.

By means of the measures in accordance with the invention, the more or less defective natural tooth crowns can be built up again in their original form, or occasionally can even be produced in a functionally still more favorable form. With the technique described, not only can the working model be produced, but also the temporary substitute can be built up rapidly and accurately. The latter serves to be placed upon the stump of the tooth as a protection against chemical and physical influences, against acids and sugar, heat and cold, for example.

The metal jacket crown finds employment as a protective crown, as a replacement crown, or as a supporting element. Here also the favorable effect of the measures in accordance with the invention becomes evident: preparation of the tooth is accomplished in known manner by removing at least 0.4 to 0.5 mm. from the tooth as covering thickness of the crown. Alternatively, jacket crowns made of porcelain or plastic require a step-by-step preparation of the tooth. In any case, the stump of the tooth is prepared, and then reproduced by the steps in accordance with the invention. The replacement piece, as the positive, is modeled by hand on the working model from well-modelable wax. When the substitute piece is finished, it likewise can be electro-optically detected and stored, possibly in three dimensional form, with great accuracy, so that a milling machine can mill the temporary substitute, or even the replacement piece, from wax with the aid of control signals, which are previously supplied to the milling machine. Their situation is governed in accordance with the prepared denture portion, but the latter, by means of the above-described measures, is already present data-wise in the form of coded control signals stored on, for example, a magnetic tape or punched tape.

Further advantages, features, and possibilities of application of the instant invention will be apparent from the ensuing description in connection with the drawings.

To make clear the device for manufacturing artificial teeth, a preferred embodiment will be described below with the aid of the photographic method according to photogrammetry.

Figure 1:
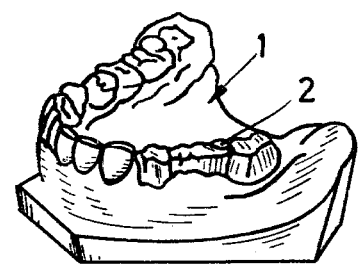
FIG. 1 shows, perspectively, a working model with a bridge placed thereon.

FIG. 1 shows, in perspective, a working model 1 of a lower jaw on which a bridge 2 is placed at front right.

Figure 2:
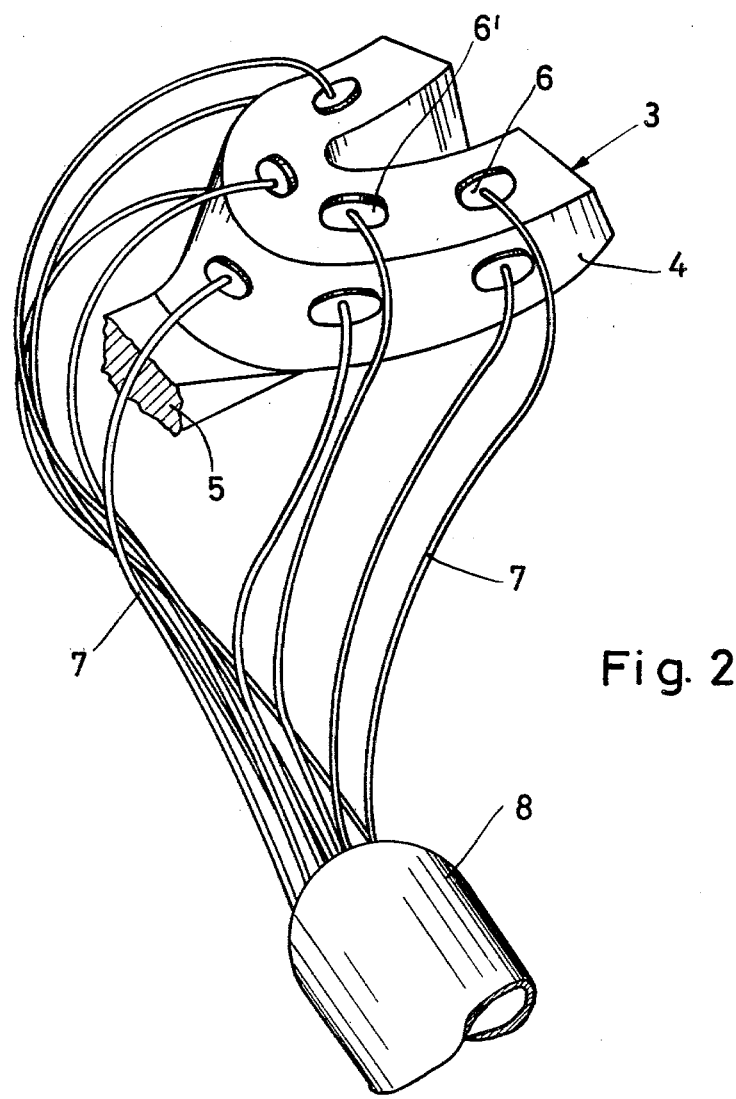
FIG. 2 shows, likely perspectively and schematically, a reproducing device with photoconductive cables.

FIG. 2 represents, in perspective, the optical reproducing device, designated generally as 3, which has a mounting 4 in the form of an impression spoon, which fits directly over the lower jaw according to FIG. 1. By means of a spoon handle 5, shown broken off, this support 4 is turned upside down over the row of teeth, with the adjacent areas. At fixed distances over all surfaces, a large number of schematically-represented lenses 6 are secured to the support 4, of which only four lenses 6 on the horseshoe-shaped surface and three lenses on the U-shaped adjacent surface are represented in the representation of FIG. 2. However, it goes without saying that suitable mountings for lenses 6 are provided from the inside—that is, from the roof of the mouth—as well as on the rear side. The lenses are optically prepared in such a manner that mutually-overlapping images of the jaw area with teeth situated directly in the vicinity are formed, so that thus the lens 6 produces a picture which overlaps, at least partially, with that of the lens 6'. This rule holds good also for all the other lenses.

Figure 3:
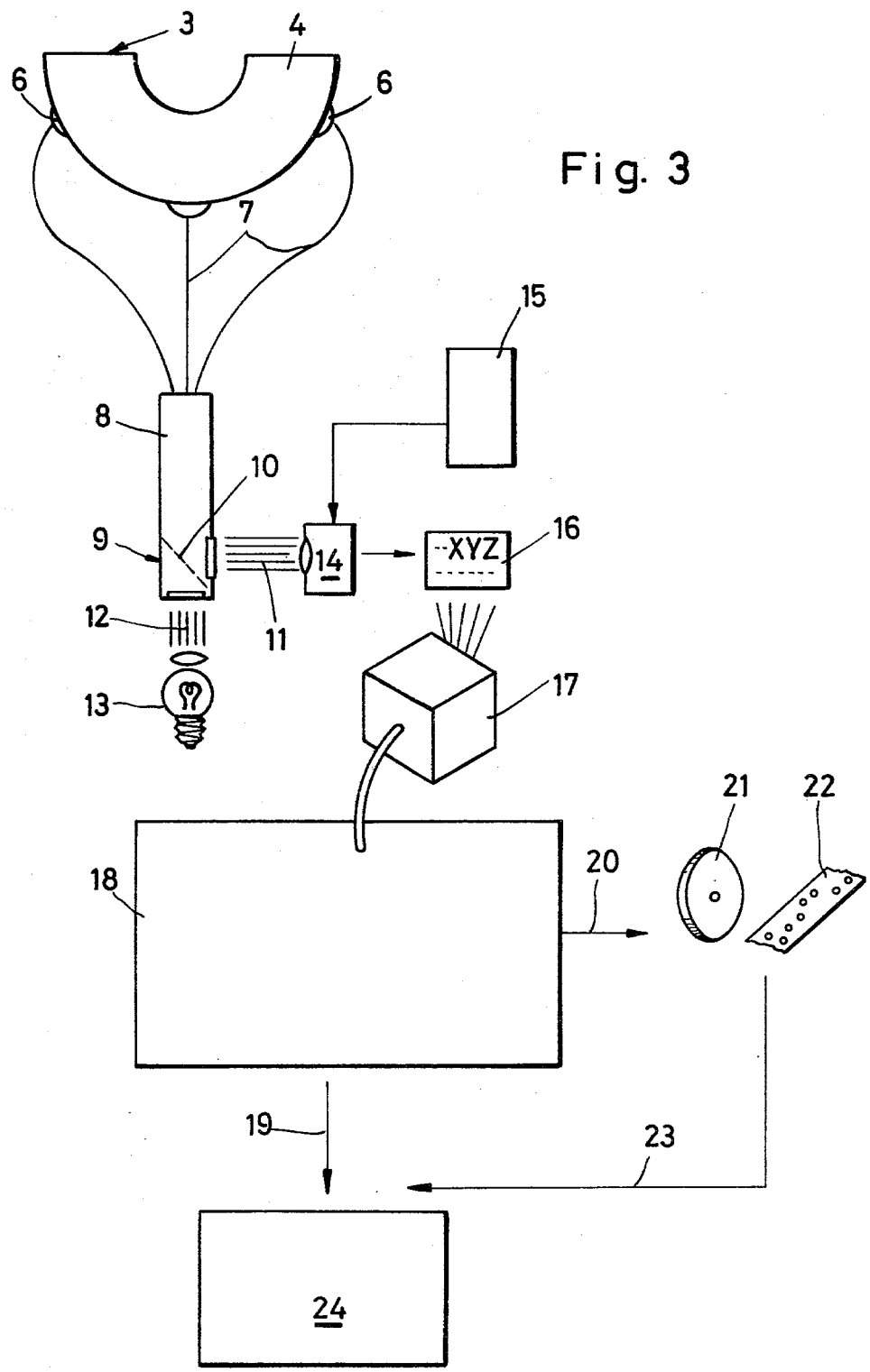
FIG. 3 shows, schematically the arrangement of the entire device.

Photo-conductive cables 7 lead from the lenses 6, 6' through a collective cable 8 to a device, represented schematically in FIG. 3 and designated generally at 9, in which a semi-reflector surface 10 permits passage-through of a portion of rays 11 and a portion of rays 12. The light source 13 generates rays 12 of light, which pass through the semi-reflector surface 10 and assure illumination of the pertinent portion of the tooth with the aid of the lenses 6, 6'. The light comes from the illuminated tooth portions through the photo-conductive cable 7 from the device 9 into the photo-apparatus 14, whose shutter is actuated by a release device 15. In this way photographic reproductions originate, which are represented schematically at 16 in FIG. 3. They are sensed by the scanning device 17 to generate surface-information signals, which then are supplied to the electronic computer 18. In the latter, the surface-information signals corresponding to the tooth stump in question are converted and arrive as electrical or magnetic control signals, either directly over the path 19 or indirectly, after being stored, over the path 20, in the magnetic tape 21 or the punched tape 22 and then, over the path 23, in an automatic milling machine 24.

Figure 4:
FIG. 4 shows, perspectively, a ground-off stump of a tooth.

Solely by way of illustration, FIG. 4 shows, in perspective, a prepared tooth stump which has a labially-ground-in cervical shoulder.

Figure 5:
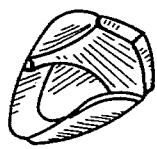
FIG. 5 shows, in perspective, a modeled replacement piece made of wax and made, of course, for another tooth stump, not for that according to FIG. 4.

In FIG. 5 is shown a wax positive modeled for another form of tooth stump. A plaster-of-paris container is formed around the latter in known manner; the wax is burned out; and then metal, preferably gold, is filled into produce an identically-shaped molded article, as shown in FIG. 5.

In accordance with the invention, milling from wax or a temporary substitute can take place without anything further with the aid of the electronically-controlled milling machine, which receives the control signals from a computer or from a storage device into which they have been fed in the above-described manner; namely, by Roentgen photography or by photogrammetry.

Figure 6:
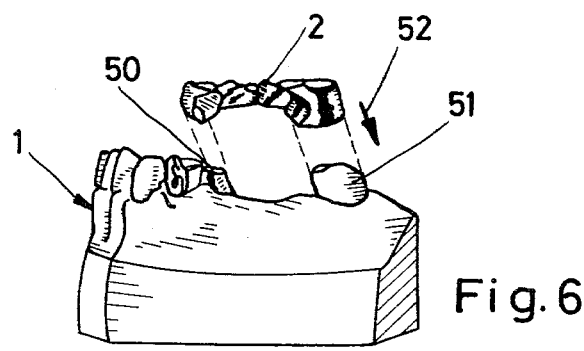
FIG. 6 shows, in perspective representation, the placing of a rather large long bridge on a working model in special parallel construction.

Finally, FIG. 6 shows, in perspective, the working model 1 in which the bridge 2 is to be set in place first. Two tooth stumps 50 and 51 will be recognized, which had to be prepared previously, precisely parallel, in correspondence to the dashed lines and in correspondence to the arrow 52. This parallel arrangement of the posts is necessary in order to make possible the incorporation of this multi-member bridge. The greater the number of posts, the more difficult it is to attain parallelity of all anchors. In accordance with the invention, however, this parallelity is attained rapidly and very accurately by the above-described measures, through the fact that the surface-information signals for an optically-visible reproduction are evaluated on a video display apparatus. With suitable enlargement, the parallelity can be checked at any time and very accurately during the preparation. In order to protect the substance of the tooth and not to damage the pulp, the exact thickness of material which is required to set the bridge 2 in place can be removed from the tooth by the simultaneous representation, for comparison purposes, of a previously-given theoretical photograph with the actual photograph.

Work in the treatment room can be carried out rapidly and precisely by use of the measures in accordance with this invention. All that is needed there is the reproducing device 3, the photo-conductive cable 7, the device 9, the light source 13, and the photo apparatus 14; also possibly the release (or extinguishing) device 15.

The photography or film or Roentgen plate designed 16 in FIG. 3 can then be evaluated, encoded, and fed into a milling machine, which then mills the desired working model or the denture from the block of material provided.

The invention also makes storage or archiving possible in a very space-saving manner, so that all data which a dentist requires relating to his patients are available for retrieval at any time. For example, in this way it is possible to make an archive (or record) of the young, undamaged bite of a patient by means of photogrammetry and then later make a denture if necessary. Also, such a comprehensive archive is of great significance in criminology.

We claim:

1. Apparatus for the manufacture of dentures in which the prepared tooth stump is reproduced in a working model, and a denture suitably conformed to the working model is formed, comprising means forming an optical reproducing device for sweeping over a tooth or tooth stump and providing an electrical output signal of three dimensional surface-information coordinates, a computer for receiving said output signal, and a milling machine operated and controlled by said computer for forming a three dimensional reproduction of said tooth or tooth stump in accordance with said surface-information coordinate signals.

2. The device of claim 1 in which said optical-recording means includes a holder in the form of an impression spoon and a plurality of lenses in said spoon, a photo-conductive cable having terminal ends associated with said lenses, a light source, a means for applying light from said source to the other end of said cable, means collecting the images from said lenses through said cable and applying the same to a photographic camera device for forming a film image thereon, and a scanning device for scanning said image and generating said surface information coordinate signals to be applied to said computer.

3. The device of claim 1 in which said light applying means and said collecting means is a half-silvered mirror.

4. The device of claim 2 in which said lenses are positioned to form mutually partially overlapping images.

5. A method useful in the manufacture of dentures in which a prepared tooth stump is reproduced in a working model and a final denture or a temporary replacement piece is suitably conformed to the working model, including the steps of
    (a) providing electro-optically produced three-dimensional surface information corresponding to the tooth stump,
    (b) converting said electro-optically produced information corresponding to the tooth stump by a computer into coordinate control signals, and
    (c) operating a milling machine automatically from said control signals to reproduce the working model of the stump from a block of material.

6. The method of claim 5 further including the steps of forming a replacement piece from a working model by providing electro-optically produced surface information corresponding to the surface of the working model, converting said electro-optically produced information corresponding to the working model into coordinate control signals by the computer, and operating the milling machine automatically from said coordinate control signals of the working model to produce a replacement piece from a block of material.

7. The method of claim 6 in which said replacement piece is a temporary replacement piece.

8. The method of claim 6 in which said replacement piece is a permanent denture.

9. The method according to claim 6 in which the working model is reproduced from surface information derived from a permanent record of surface information of the patient's original tooth configuration.

10. The method of claim 9 in which the surface information is derived from Roentgen photography.

11. The method according to claim 5, claim 6 or claim 7 in which a permanent reproducible record is made of the control signals applied to the milling machine.

12. The method in accordance with claims 5, 6, 7 or 8, further including the step of providing a video display of the surface information corresponding to the working model for the purpose of comparison.

13. The method for the manufacture of dentures in which a prepared tooth stump is reproduced in a working model, and a denture or replacement piece is suitably conformed to the working model, comprising the steps of photogrammetrically deriving surface information of the desired tooth configuration, converting said photogrammetrically supplied surface information to control signals for the operation of a milling machine, and milling the denture or replacement piece from a block of material in accordance with said control signals.

14. The method according to claim 12 in which said photogrammetrically reproduced information is retained in a permanent record such as a magnetic or a video tape.

15. The method according to claim 12 in which said photogrammetrically reproduced information is obtained from a permanent record of the patient's original teeth.

16. The method of claim 12 further including the step of providing a video display of the photogrammetrically produced surface information for the purpose of comparison.

* * * * *